United States Patent [19]
Reese

[11] 3,951,133
[45] Apr. 20, 1976

[54] DEVICE TO DISPLAY SKIN TEMPERATURE CHANGES BY CHANGES IN COLOR

[76] Inventor: John P. Reese, 400 Governors Drive, No. 9, Winthrop, Mass. 02152

[22] Filed: Sept. 12, 1974

[21] Appl. No.: 505,357

[52] U.S. Cl. ................................. 128/2 H; 73/356
[51] Int. Cl.² ................. A61B 10/00; G01K 11/16
[58] Field of Search ................... 128/2 H; 73/356; 23/230 LC

[56] References Cited
UNITED STATES PATENTS

| | | | |
|---|---|---|---|
| 3,175,401 | 3/1965 | Geldmacher | 73/356 X |
| 3,465,590 | 9/1969 | Kluth et al. | 73/356 |
| 3,524,726 | 8/1970 | De Koster | 73/356 X |
| 3,633,425 | 1/1972 | Sanford | 73/356 |
| 3,661,142 | 5/1972 | Flam | 128/2 H |
| 3,765,243 | 10/1973 | Pickett et al. | 73/356 |
| 3,830,224 | 8/1974 | Vanzetti et al. | 128/2 H |

*Primary Examiner*—Kyle L. Howell
*Attorney, Agent, or Firm*—Wolf, Greenfield & Sacks

[57] ABSTRACT

Two or more sheets of liquid crystal thermal film assembled side by side, one surface of which assembly is covered by a flat piece of temperature equalizing material made of high thermal conductivity material, such as tin-foil, which film sheets change color in response to changes in the skin temperature of a person on whom my device is attached. At opposite sides of the sheets are two retaining strips of material to wrap around a finger, that can be fastened together or unfastened as desired.

1 Claim, 8 Drawing Figures

DEVICE TO DISPLAY SKIN TEMPERATURE CHANGES BY CHANGES IN COLOR

The principal object of my invention is to show a patient or a doctor by changes in color, when a patient's skin temperature changes. For instance, when a certain sheet of film changes to a certain color, a relaxation of tension is indicated due to a rise in temperature of the skin covered by my device.

OBJECTS OF THE INVENTION

Another object is to form my device of readily available materials, small quantities of which are sufficient, and which can be assembled in simple steps by unskilled labor.

The foregoing and other objects which will appear as the nature of the invention is better understood, may be accomplished by a construction, combination and arrangement of parts such as is disclosed by the drawing. The nature of the invention is such as to render it susceptible to various changes and modifications, and therefore, I am not to be limited to the construction disclosed by the drawing nor to the particular parts described in the specification, but am entitled to all such changes therefrom as fall within the scope of my invention.

As illustrated, my device 10 has a plurality of color changing, film sheets such as liquid crystal thermal film, three being shown, identified by the numerals 12, 14 and 16, forming a film assembly 15. Two sheets may sometimes serve the purpose, as may four or more. These sheets may very in size, as, for instance for a finger each sheet may measure 11/16 inch long and 3/16 inch wide.

Figure 6:
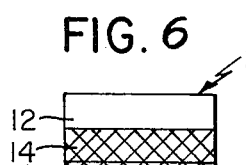
FIG. 6 is an enlarged plan view of the film assembly, the sheets of said film indicating their colors at relatively low range of temperatures.
Figure 7:
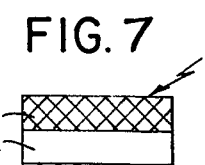
FIG. 7 is a view similar to FIG. 6 indicating the colors of film sheets at an intermediate range of temperatures.
Figure 8:
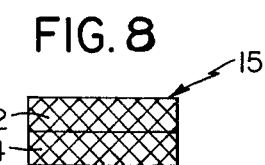
FIG. 8 is a view similar to FIG. 6 indicating the colors of film sheets at a higher range of temperatures.

Sheet 12 is intended to respond by changing color at a temperature between 66° and 77°F., for instance, while sheet 14 responds by changing color at a temperature between 77° and 86°F. and sheet 16 so responds at a temperature between 86° and 98°F. See illustration in FIGS. 6, 7 and 8 of the drawings. These are but examples, as my invention is applicable at greater or lesser temperatures.

On the rear or inner surface of said three sheets is a heat conductor sheet 18 formed of foil, of high thermal conductivity, which is attached, as by an adhesive 17, and which covers all face surfaces of said sheets, thus forming an integral flat piece 19. This sheet 18, in use, contacts a person's skin directly, preferably at the inner surface of the latter. It is a heat equalizing and distributing means, and increases the display area of said film sheets by distributing the heat to a larger area evenly, as otherwise without said conductor sheet 18 the temperature variations over small areas of skin, would result in presenting a splotch of colors that would be difficult to gain an accurate reading therefrom.

Figure 1:
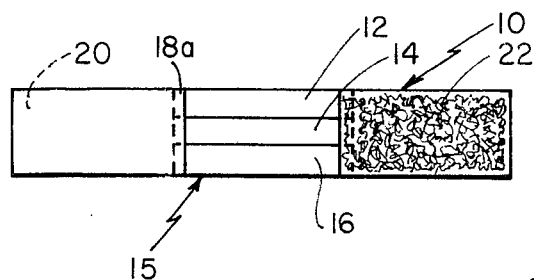
FIG. 1 is a plan view of my device, when laid out flat with the film sheets uppermost.
Figure 3:
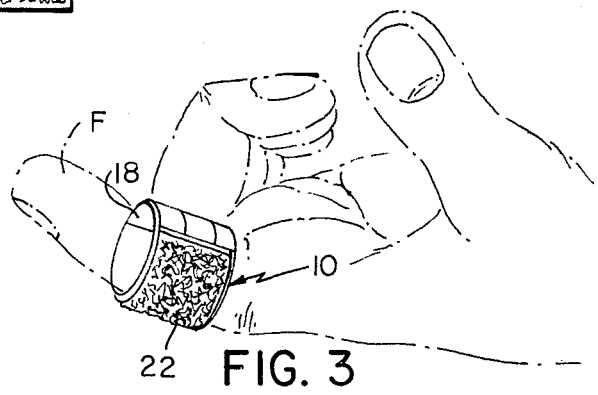
FIG. 3 is a perspective view showing my device in position of use on a finger, the latter and part of a hand being shown in dot and dash lines.
Figure 2:
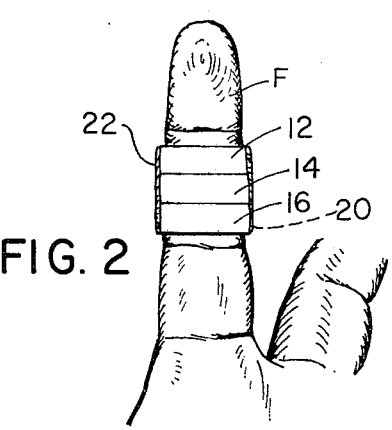
FIG. 2 is an elevational view showing my device in position of use on a person's finger.
Figure 4:
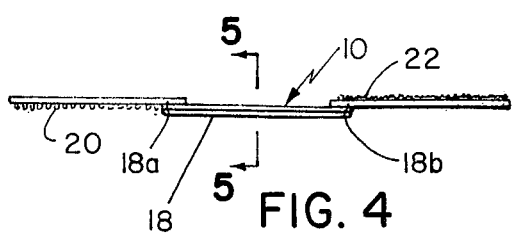
FIG. 4 is an edge elevational view of my device.
Figure 5:
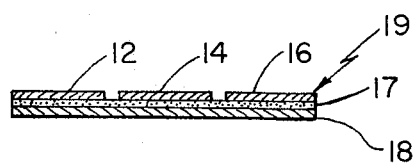
FIG. 5 is an enlarged, sectional view taken on the line 5—5 of FIG. 4.

In use, my device, may be wrapped around a person's finger F with said foil sheet 18 in contact with the inside of the finger, as shown, between the knuckle joint and joint nearest the finger-nail as illustrated in FIGS. 2 and 3. It is held there by two well-known retainers, which may be an elastomeric type or otherwise, one said retainer 20 having an overlapping edge portion 18a and another said retainer 22 having an overlapping edge portion 18b. Said film assembly 15 is attached at opposite sides to said overlapping portions 18a and 18b.

In use, my device is brought into contact with a person's skin, as by wrapping around a finger, as above explained, or a toe. Ordinarily said film sheet 12 will promptly respond by changing color, as from black to brown to blue, for instance. At a further change as to a point between 77 and 86 degrees F. in the temperature of the skin, said film sheet 14 will further respond, by changing colors, as from green to blue to show a rise in skin temperature. When the film sheet 16 shows a change in color as from dark green to dark blue, it indicates that not only has the skin temperature further risen higher, somewhere between 86° and 98°F. for instance; but that the person has further relaxed from his first condition. The foregoing are given as examples only, as colors may vary otherwise, responding to other skin temperatures.

These changes in temperature of the skin as well as the display of colors, as aforesaid, indicate, as the skin temperature rises, that the person's health condition has improved. For instance, one suffering from a migraine headache, will enjoy progressive relief as he relaxes, and it is helpful in a person's illness, to both a physician and a patient, by the variety of colors displayed on different film sheets, that relaxation is taking place.

What I claim is:

1. A device that displays skin temperature changes and that is worn by a person about a finger or toe, said device comprising:

a plurality of relatively thin color-changing liquid crystal thermal film sheets, a first of said film sheets being color responsive to changes in the temperature of the skin of the person between a limited range of temperatures of the skin, a second of said film sheets being responsive to changes in the temperature of the skin of the person between a second limited range of temperatures of the skin that is higher than said first range of temperatures and a third of said film sheets being responsive to changes in the skin temperature of a person at a temperature higher than said second range of temperatures, a relatively thin metal heat conductor sheet, means for attaching a face surface of said film sheets to the conductor sheet with the three film sheets being disposed abutting each other, extending substantially parallel to each other and each being of somewhat elongate rectangular shape substantially totally covering the conductor sheet with said first, second and third film sheets being disposed in successive order, said film sheets changing color substantially mutually exclusively and in a reversible manner with the total area covered by all sheets being about the same as the area covered by the conductor sheet, and retaining means attached to the assembly of film sheets and conductor sheet to hold the conductor sheet to the surface of the skin of the person, said retaining means including two separate retainer strips and means for securing the strips respectively, to opposite relative thin borders of the assembly wherein the borders are each defined by successive ends of the film sheets with each retainer strip being slightly overlapped with each such border of the film sheets, wherein said retainer strips attached to a side of said film sheets opposite to said conductor sheet.

* * * * *